United States Patent
Silverman et al.

(10) Patent No.: US 6,274,557 B1
(45) Date of Patent: Aug. 14, 2001

(54) INHIBITION OF NITRIC OXIDE SYNTHASE BY AMINO ACIDS AND DIPEPTIDES

(75) Inventors: Richard B. Silverman, Northbrook; Hui Huang, Evanston; Henry Q. Zhang, Grayslake, all of IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 09/428,247

(22) Filed: Oct. 27, 1999

Related U.S. Application Data

(63) Continuation of application No. PCT/US98/07037, filed on Apr. 8, 1998.
(60) Provisional application No. 60/062,668, filed on Oct. 8, 1997, and provisional application No. 60/045,192, filed on Apr. 30, 1997.

(51) Int. Cl.[7] .................................................. C07K 5/06
(52) U.S. Cl. ............................ 514/19; 562/560; 514/20
(58) Field of Search ........................ 514/19; 562/560; 435/184

(56) References Cited

U.S. PATENT DOCUMENTS

| | | | | |
|---|---|---|---|---|
| 4,370,318 | * | 1/1983 | Umezawa | 424/177 |
| 4,395,401 | * | 7/1983 | Pfeiffer | 424/177 |
| 4,518,587 | * | 5/1985 | Laruelle | 514/19 |
| 5,225,440 | | 7/1993 | London et al. | 514/535 |
| 5,332,726 | * | 7/1994 | Klein | 514/18 |
| 5,468,476 | * | 11/1995 | Ahluwalia | 424/73 |
| 5,545,614 | | 8/1996 | Stamler et al. | 514/6 |
| 5,621,004 | * | 4/1997 | Dunn | 514/551 |
| 5,837,687 | * | 11/1998 | Nakashima | 514/18 |
| 5,869,526 | * | 2/1999 | Makino | 514/508 |

OTHER PUBLICATIONS

Akhtar et al., *Biochemistry,* 33(14), 4410–4418 (1994).
Bhargava, *Gen. Pharmacol.,* 26, 1049–1053 (1995).
Burnett et al., *Science,* 257, 401–403 (1992).
Choi et al., *Annu. Rev. Neurosci.,* 13, 171–182 (1990).
Choi, *J. Neurosci.,* 10(8), 2493–2501 (1990).
Cornish–Bowden, *Biochem. J.,* 137, 143–144, 1974.
Crane et al., *Science,* 278, 425–431 (1997).
Crossin, *Trends Biochem. Sci.,* 16, 81–82 (1991).
Das et al., *Biochem. Biophys. Res. Commun.,* 212(2), 375–380 (1995).
Dixon, *Biochem. J.,* 55, 170–171 (1953).
Dorheim et al., *Biochem. Biophys. Res. Commun.,* 205(1), 659–665 (1994).
Dwyer et al., *Biochem. Biophys. Res. Commun.,* 176(3), 1136–1141 (1991).
Fasehun et al., *Faseb J.,* 4, A309 (1990).
Fast et al., *Bioorg. & Med. Chem. Lett.,* 7(11), 1449–1454 (1997).
Fast et al., *Bioorg. & Med. Chem.,* 5, 1601–1608 (1997).
Feelish et al., *Eur. J. Pharmacol.,* 139, 19–30 (1987).
Feldman et al., *Chem. Eng. News,* 71, 26–38 (1993).
Feldman et al., *J. Med. Chem.,* 36, 491–496 (1993).
Ferrendelli et al., *Brain Res.,* 200, 93–103 (1980).
Furifne et al., *Biochemistry,* 32, 8512–8517 (1993).
Furfine et al., *J. Biol. Chem.,* 269, 26677–26683 (1994).
Garthwaite, in *NMDA Receptor,* Watkins & Collingridge Ed., Oxford University Press; Oxford, England; 187–205 (1989).
Garvey et al., *J. Biol. Chem.,* 269(43), 26669–26676 (1994).
Gross et al., *Biochem. Biophys. Res. Commun.,* 170(1), 96–103 (1990).
Hecker et al., *FEBS Lett.,* 294(3), 221–224 (1991).
Hevel et al., *Methods Enzymol.,* 233, 250–258 (1994).
Hevel et al., *J. Biol. Chem.,* 266, 22789–22791 (1991).
Hofmann et al., *Biochemistry,* 34, 13443–13452 (1995).
Iyengar et al., *Proc. Natl. Acad. Sci. USA,* 84, 6369–6373 (1987).
Kerwin et al., *Med. Res. Rev.,* 14, 23–74 (1994).
Kerwin et al., *J. Med. Chem.,* 38(22), 4342–4362 (1995).
Kubes et al., *Proc. Natl. Acad. Sci. USA,* 88, 4651–4655 (1991).
Lambert et al., *Life Sciences,* 48, 69–75 (1991).
MacIntyre et al., *Proc. Natl. Acad. Sci. USA,* 88, 2936–2940 (1991).
Marletta, *J. Biol. Chem.,* 268(17), 12231–12234 (1993).
Marletta, *J. Med. Chem.,* 37(13), 1899–1907 (1994).
Martasek et al., *Biochem. Biophys. Res. Commun.,* 219, 359–365 (1996).
McCall et al., *Br. J. Pharmacol.,* 102, 234–238 (1991).
Moore et al., *J. Med. Chem.,* 37, 3886–3888 (1994).
Moore et al., *Bioor. Med. Chem.,* 4, 1559–1564 (1996).
Moore et al., *J. Med. Chem.,* 39, 669–672 (1996).
Nakane et al., *Mol. Pharmacol.,* 47, 831–834 (1995).
Olken, *J. Med. Chem.,* 35, 1137–1144 (1992).
Olken et al., *Biochemistry,* 32, 9677 (1993).
Olken et al., *Biochemistry,* 33, 14784–14791 (1994).
Osawa et al., *Biochem. Biophys. Res. Commun.,* 194, 1435–1439 (1993).
Palmer et al., *Nature,* 327, 524–526 (1987).
Ross et al., *Trends Neurosci.,* 13, 216–222 (1990).
Seo et al., *Arch Biochem. Biophys.,* 324, 41–47 (1995).
Sheta et al., *J. Biol. Chem.,* 269(21), 15147–15153 (1994).
Shibuki et al., *Nature,* 349, 326–328 (1991).
Silverman et al., *J. Med. Chem.,* 40, 2813–2817 (1997).
Stuehr et al., *Adv. Enzymol.,* 65, 287–346 (1992).
Thomsen et al, *CNS Drugs,* 2(6), 417–422 (1994).
White et al., *Biochemistry,* 31(29), 6627–6631 (1992).
Wolff et al., *Arch. Biochem. Biophys.,* 311, 293–299 (1994).
Wolff et al., *Arch. Biochem. Biophys.,* 311, 300–306 (1994).
Wolff et al., *Arch. Biochem. Biophys.,* 316, 290–201 (1995).
Wolff et al., *Arch. Biochem. Biophys.,* 325, 227–234 (1996).
Zhang et al., *J. Med. Chem.,* 40, 3869–3870 (1997).
Zhang et al., *J. Am. Chem. Soc.,* 119, 10888–10902 (1997).

* cited by examiner

*Primary Examiner*—Christopher S. F. Low
*Assistant Examiner*—David Lukton
(74) *Attorney, Agent, or Firm*—Leydig, Voit & Mayer, Ltd.

(57) ABSTRACT

Methods and compositions for inhibiting at least one isoform of nitric oxide synthase are provided. Pharmaceutical compositions include derivatives of arginine as well as dipeptides and dipeptide analogs that contain nitroarginine or another unnatural amino acid. Compositions can be used to selectively inhibit particular isoforms of nitric oxide synthase.

7 Claims, No Drawings

INHIBITION OF NITRIC OXIDE SYNTHASE BY AMINO ACIDS AND DIPEPTIDES

This application is a continuation of international application PCT/US98/07037, filed Apr. 8, 1998, and claims priority to U.S. Provisional Patent Applications Ser. Nos. 60/045,192 and 60/062,668, filed on Apr. 30, 1997 and Oct. 8, 1997, respectively. The disclosures of both those applications are incorporated herein by reference.

OWNERSHIP RIGHTS IN PATENT

Funds used to support the studies disclosed herein were provided in part by the United States Government (NIH-GM 49725 and NIH-CA 50414 and NIH-GM 52419). The United States Government, therefore, may retain rights in this invention.

TECHNICAL FIELD OF THE INVENTION

The field of this invention is enzymology. More particularly, this invention relates to amino acid, dipeptide, and dipeptide analog inhibitors of nitric oxide synthase.

BACKGROUND OF THE INVENTION

Nitric oxide (NO) has been shown to be an important biological second messenger which is biosynthesized by a family of enzymes called nitric oxide synthases (EC 1.14.13.39). Three principal isoforms of this enzyme have been isolated and characterized, each associated with different physiological functions. (Kerwin, J. F.; Lancaster, J. R., J. R. Jr.; Feldman, P. L., J. Med. Chem. 1995, 38, 432–62.) As is well known in the art, there are numerous isoforms of NOS. Those isoforms are designated herein as endothelial NOS (eNOS), neuronal NOS (nNOS) and inducible NOS (iNOS). The isoform from endothelial cells (eNOS) is involved in the regulation of smooth muscle relaxation, blood pressure lowering, and inhibition of platelet aggregation. Neuronal nitric oxide synthase (nNOS) is important for long-term potentiation, and an inducible form (iNOS), which acts in host defense, is generated by activated macrophage cells during an immune response. The endothelial and neuronal isoforms are expressed constitutively and require $Ca^{2+}$ and calmodulin for activity; the macrophage form is induced by cytokines or bacterial lipopolysaccharides and is $Ca^{2+}$ and calmodulin independent. All forms of the enzyme require NADPH, tetrahydrobiopterin, heme, and at least FAD if not both FAD and FMN.

Despite the extraordinary importance of NO to the apparent health of organisms, it also has been associated with a large number of harmful effects as a result of its reactive free radical properties; in fact, NO has a lifetime of only a few seconds at physiological pH and temperature. Overproduction of NO, consequently, has been implicated in a wide variety of diseases (Kerwin, J. F.;

Heller, M. The Arginine-Nitric Oxide Pathway: A Target for New Drugs. Med Res. Rev. 1994, 14,23–74). NO overproduction by nNOS has been implicated in strokes, septic shock, seizures, schizophrenia, migraine headaches, Alzheimer's disease, long-term depression, and priapism. (Choi, D. W.; Rothman Annu. Rev. Neurosci, 1990, 13, 171–182, Garthwaite, J. In the NMDA Receptor; Watkins, J. C. Collingridge G. L. Ed.: Oxford University Press; Oxford England; 1989, pp. 187–205; Crossin, K. L. Trends Biochem. Sci, 1991, 16, 81–2; Kerwin, J. F.; Lancaster, J. R., J. R. Jr.: Feldmand, P. L. 1995,38,432–62. J. Med. Chem; Das, I.; Khan, N. S.; Puri, B. K.; Sooranna, S. R.; de Belleroche, J.; Hirsch, S. R. Biochem. Biophys. Res. Commun. 1995, 212, 375–380.; Thomsen, L. L.; Iversen, H. K.; Lassen, L. H.; Olesen, J. CYS Drugs 1994, 2, 417–22.; Dorheim, M. A.; Tracey, W. R.; Pollock, J. S.; Grammas, P. Biochem. Biophys. Res. Commun. 1994,205, 659–665.; Shibuki, K.; Okada, D. Nature 1991, 349, 326–328.; Burnett, A. L.; Lowenstein, C. J.; Bredt, D.S.; Chang, T. S. K.; Snyder, S. H. Science 1992,257,401–403). iNOS overproduction of NO has been associated with tolerance to and dependence on morphine, development of colitis, tissue damage and inflammation, overproduction of osteoclasts, leading to osteoporosis, Paget's disease, rheumatoid arthritis, and destruction of photoreceptors in the retina. (Bhargava, H. N. Gen. Pharmacol. 1995, 26, 1049–1053).; Seo, H. G.; Takata, I.; Nakamura, M.; Tatsumi, H.; Suzuki, K.; Fujii, J.; Taniguchi, N. Arch. Biochem. Biophys. 1995, 324, 41–47., Kubes, P.; Suzuki, M.; Granger, D. N. Proc. Natl. Acad. Sci. USA 1991, 88, 4651–4655; MacIntyre, I.; Zaidi, M.; Towhidul Alam, A. S. M.; Datta, H. K.; Moonga, B. S.; Lidbury, P. S.; Hecker, M.; Vane, J. R. Proc. Natl. Acad. Sci. USA 1991, 88,2936–2940; and Ross, C. A.; Bredt, A.; Snyder, S. H. Trends Neurosci. 1990, 13, 216–22. This suggests that inhibition of NOS would have a significant beneficial effect on disease states arising from the overproduction of NO.

A wide variety of compounds have been shown to inhibit NOS, (Marlett, M. A. J. Med. Chem. 1994, 37, 1899–1907; Moore, W. M.: Webber, R. K. Fok, K. F.; Jerone, G. M.: Kornmeier, C. M.; Tjoeng, F. S.; Currie, M. G. Bioorg. Med. Chem 1996. 4. 1559–1564). However, because of the general importance of NO to human health, selective inhibition of the isoforms of NOS is essential. Selectivity for the three isoforms already has been reported to some degree. The early inhibitors were analogs of L-arginine. $N^{\omega}$-Methyl-L-arginine and $N^{\omega}$--ethyl-L-arginine, however, show only about a factor of 2 selectivity; $N^{\omega}$--methyl-L-arginine is selective for eNOS and nNOS over iNOS and $N^{\omega}$--ethyl-L-arginine is selective for iNOS over nNOS and eNOS. (Moore, W. M.; Webber, R. K.; Fok, K. F.; Jerone, G. M.; Connor, J. R.; Manning, P. T.; Wyatt, P. S.; Misko, R. P.; Tjoeng, F. S.; Currie, M. G. J. Med. Chem. 1996. 39. 669–72). $N^{\omega}$--Nitro-L-arginine is about 300-fold selective for nNOS over iNOS (Furfine, E. S.; Harmon, M. F.; Paith, J. E.; Garvey, E. P. Biochemistry, 1993, 32, 8512–8517). 2-Amino-5,6-dihydro-6-methyl-4H-1,3-thiazine and S-ethylisothiourea were termed "potent and selective inhibitors,: but had only 10–40 fold selectivity in favor of iNOS (Furfine, E. S.; Harmon, M. F.; Paith, J. E.; Garvey, E. P. Biochemistry, 1993, 32, 8512–8517; Nakane, M.; Klinghofer, V.; Kuk, J. E.; Donnelly, J. L.; Budzik, G. P.; Pollock, J. S.; Basha, F.; Carter, G. W. Mol. Pharmacol. 1995, 47, 831–4. 2-Iminoazaheterocycles showed selectivities of 1.1–9 in favor in iNOS over eNOS and nNOS (Moore, W. M.; Webber, R. K.; Fok, K. F.; Jerone, G. M.; Connor, J. R.; Manning, P. T.; Wyatt P. S.; Misko, R. P.; Tjoeng, F. S.; Currie, M. G. J. Med. Chem. 1996, 39, 669–72). Various indazole analogs had selectivities of 5–10 for either nNOS or iNOS. (Wolff, D. J.; Grivin, B. J. Arch. Biochem. Biophys. 1994, 311, 300–306). Imidazole analogs exhibited selectivities in the range of 3–6 fold in favor of iNOS; (Wolff, D. J.; Gribin, B. J. Arch. Biochem. Biophys. 1994, 311, 293–9). Aminoguanidine shows a 50-fold selectivity for iNOS over nNOS and 500-fold over eNOS (Wolff, D. J.; Lubeskie, Arch. Biochem. Biophys. 1995, 316, 290–301). Several "potent and selective" series of isothiourea analogs favored inhibition of iNOS over eNOS by factors of between 2- and 6-fold with one analog being 19-fold selective; bisisothioureas were more selective with one analog showing a selectivity of 190-fold in preference of iNOS, (Wolff, D. J.; Lubeskie,. *Arch. Biochem. Biophys.* 1995, 316, 290–301). S-Methyl- and S-ethyl-L-thiocitrulline, also called "potent and selective," were 10- and 50-fold, respectively, more selective for nNOS than eNOS (Furfine, E. S.; Harmon, M. F.;. Paith, J. E.; Knowles, R. G.; Salter, M.; Kiff, R. J.; Duffy, C.; Hazelwood, R.; Oplinger, J. A.; Garvey, E. P. *J. Biol. Chem.* 1994, 269, 26677–83), L-N$^6$-(1-Iminoethyl)lysine, another "selective" inhibitor of NOS favors the inhibition of iNOS by a factor of 30 over eNOS and by 13 over nNOS (Moore, W. M.; Webber, R. K.; Jerone, G. M.; Tjoeng, F. S.; Misko,. T. P.; Currie, M. G. , *J. Med. Chem.* 1994, 37, 3886–8).

Because of the relatively high selectivity of $N^\omega$--nitro-L-arginine for nNOS over iNOS, and the observation that it is a time-dependent inhibitor of nNOS, but a reversible inhibitor of iNOS (Dwyer, M. A.; Bredt, D. S.; Snyder, S. H. *Biochem. Biophys. Res. Commun.* 1991, 176, 113641) it was decided to determine if $N^\omega$--nitroarginine-containing dipeptide esters or amides would have increased selectively for nNOS. Since L-arginine methyl ester, L-argininamide, and L-arginine-containing dipeptides are substrates for NOS it was thought that the dipeptide esters or amides may be functional as well. Furthermore, the fact that $N^\omega$--nitro-L-arginine inhibits nNOS in vivo following intraperitioneal injection suggests that it crosses the blood-brain barrier, even though L-arginine poorly crosses (Hecker, M.; Walsh D. T.; Vance, J. R. On the substrate specificity of nitric oxide synthase. *FEBS Lett.* 1991, 294, 2214). This may be the result of the decrease in pKa of the guanidino group because of nitro substitution.

BRIEF SUMMARY OF THE INVENTION

In one aspect, the present invention provides a method of inhibiting the activity of at least one isoform of NOS. In accordance with that method, one or more isoforms of NOS are exposed to an effective inhibitory amount of an amino acid derivative of Arg or a dipeptide that contains an unnatural amino acid residue. Isoforms of NOS that can be inhibited by the present process include eNOS, nNOS and iNOS. In a first embodiment, inhibition of NOS activity is accomplished using an $N^\omega$--alkyl-L-Arg. A preferred alkyl is propyl. $N^\omega$--propyl-L-Arg inhibits the activity of nNOS to a greater extent than the activity of both eNOS and iNOS. The inhibition of eNOS is greater than the inhibition of iNOS. Thus, $N^\omega$--propyl-L-Arg can be used to selectively inhibit nNOS relative to both eNOS and iNOS and to selectively inhibit eNOS relative to iNOS.

In a second embodiment, the method uses a dipeptide that contains at least one $N^\omega$-nitroArg or other unnatural amino acid residue. Preferably, the dipeptide contains only one such residue. The unnatural amino acid residue can be located at either the N- or C-terminus of the dipeptide and can be in either the D- or L-configuration. In a preferred embodiment, the N-terminal residue is $N^\omega$-L-nitroArg. In another preferred embodiment, the C-terminal residue is $N^\omega$-D-nitroArg. Where there is only one unnatural amino acid residue, the other residue can be any natural amino acid residue. The other residue can also be in either the D- or L-configuration. The dipeptide can be in the form of an ester, an amide, or other peptidomimetic group.

In one preferred embodiment, the dipeptide contains $N^\omega$-nitroArg residue and Phe. Dipeptides having L-nitroArg at the N-terminus favor inhibition of nNOS activity over inhibition of iNOS and eNOS activity. When the dipeptide has an L-Phe at the N-terminus, inhibition of iNOS activity is greater than inhibition of nNOS and eNOS activity. Benzyl ester dipeptides inhibit iNOS activity to a greater extent than nNOS and eNOS activity. Methyl ester dipeptides that contain a D-amino acid, however, exhibit an inhibitory preference for nNOS over iNOS and eNOS. Especially preferred dipeptides that contain nitroArg and Phe are D-Phe-L-nitroArg, L-nitroArg-L-Phe, L-nitroArg-L-Phe-OMe, L-nitroArg-L-Phe-OMe, D-nitroArg-D-Phe-OMe, D-Phe-L-nitroArg-OMe, L-Phe-D-nitroArg-OMe, or D-Phe-D-nitroArg-OMe.

In another preferred embodiment, the dipeptide is a dipeptide amide that contains one $N^\omega$-nitroArg and a second residue other than $N^\omega$-nitroArg or Phe. Where the dipeptide contains $N^\omega$-nitroarginine at the C-terminus, the inhibition of eNOS and nNOS activity is greater than the inhibition of iNOS activity. Especially preferred such peptides are $N^\omega$-L-nitroarginine-L-Lys, N-L-nitroArg-$N^\omega$-L-nitroArg, L-Lys-$N^\omega$-D-nitroArg, D-Lys-$N^\omega$-D-nitroArg, L-His-N-D-nitroArg, $N^\omega$-L-nitroArg-D-Glu, $N^\omega$-D-nitroArg-L-Ser, and $N^\omega$-L-nitroArg-D-Asn, $N^\omega$-L-nitroArg-L-Dpr, $N^\omega$-L-nitroArg-L-Dbu, $N^\omega$-nitroArg-L-Orn, $N^\omega$-D-nitroArg-L-Dbu, $N^\omega$-L-nitroArg-D-Orn, L-Dbu-$N^\omega$-D-nitroArg; L-Orn-$N^\omega$-D-nitroArg and D-Om-$N^\omega$-D-nitroArg. Where the dipeptide contains $N^\omega$-nitroArg at the N-terminus, nNOS activity is inhibited to a greater extent than eNOS and iNOS activities. Preferably the $N^\omega$-nitroarginine is L-$N^\omega$-nitroarginine.

The present invention further provides pharmaceutical compositions that contain an inhibitor of the present invention.

DETAILED DESCRIPTION OF THE INVENTION

I. The Invention

The present invention provides amino acid and dipeptide inhibitors of nitric oxide synthase (NOS), pharmaceutical compositions containing those amino acids or dipeptides and methods of inhibiting at least one isoform of NOS activity using those amino acids or dipeptides. As disclosed hereinafter, certain of the inhibitors are selective for one or more isoforms of NOS.

II. Amino Acid Inhibitors

In one aspect, the present invention provides derivatives of the amino acid arginine (Arg) that inhibit NOS. A derivative of arginine in accordance with this invention has the formula N-R-Arg, where R is a $C_1$–$C_6$ alkane or alkene. The alkane or alkene can be a linear, branched or cyclic alkane or alkene. In a preferred embodiment, R is lower alkyl. An especially preferred alkyl is propyl. As shown hereinafter in the Examples, $N^\omega$-Propyl-L-arginine was found to be a competitive inhibitor of all three isoforms, eNOS, nNOS and iNOS. On the basis of the K values with each isoform, it is apparent that there is a considerable degree of selectivity in favor of nNOS. The potency of inhibition of nNOS by $N^\omega$-propyl-L-arginine is 3158 times that of iNOS and 149-fold that of eNOS. This nNOS/iNOS selectivity is one of the largest, if not the largest, degree of selectivity reported for nNOS. The selectivity of nNOS over eNOS also is fairly substantial. This is quite unexpected, given that the selectivity factors for $N^\omega$-methyl-L-arginine and $N^\omega$-ethyl-L-arginine are only about 2. $N^\omega$-Ethyl-L-arginine is slightly selective for iNOS over nNOS and eNOS. Furthermore, putting unsaturation into the propyl side chain has a dramatic, undesirable effect on selectivity. Both N-allyl-L-arginine and $N^\omega$-propargyl-L-arginine are weakly selective, the former having a selectivity of nNOS/ iNOS of about 10 and nNOS/eNOS of 15, whereas the latter has a selectivity of less than 2. It is apparent that the geometry and size of the side chain is extremely important to the selectivity of inhibition.

II. Dipeptide and Related Inhibitors of NOS

In another aspect, the present invention provides dipeptide inhibitors of at least one isoform of NOS. A dipeptide of the present invention contains at least one and, preferably only one, unnatural amino acid residue. As used herein, the phrase "unnatural amino acid" means, as is well known in the art, an amino acid other than the twenty naturally occurring amino acids (e.g., nitroLys), ornithine (Orn), 2,4-diaminobutanoic acid (Dbu), 2,3-diaminopropanoic acid (Dpr) and substituted arginines. The substituent group on Arg is preferably a $C_1$–$C_6$ alkane or alkene. The substituent group can be linear, branched or cyclic. A preferred substituent group for Arg is alkyl. The single $N^\omega$-nitroArg can be located at either the N- or C-terminus of the dipeptide. The $N^\omega$-nitroArg can be either $N^\omega$-D-nitroArg or $N^\omega$-L-nitroArg.

Any naturally occurring or unnatural amino acid can be the other residue in the dipeptide. That other residue can also be in either the D- or L-configuration. In one embodiment, the other residue of the dipeptide is phenylalanine (Phe). A series of $N^\omega$-nitroarginine- and phenylalanine-containing dipeptides and dipeptide esters were synthesized as potential selective inhibitors of neuronal nitric oxide synthase (nNOS). All of the dipeptides that contain $N^\omega$-L-nitroArg were competitive inhibitors of nNOS, iNOS and eNOS activity. Dipeptides that contain D-nitroArg were uncompetitive inhibitors of iNOS, but competitive inhibitors of NNOS and eNOS. None of the dipeptides or dipeptide esters tested exhibited time-dependent inhibition of any of the NOS isoforms. The order of the amino acids in the dipeptide and the chirality of the amino acids are both important to selectivity. A detailed description of the inhibitory effects of nitroArg-Phe dipeptides is set forth hereinafter in the Examples.

An entire series of dipeptide amides containing $N^\omega$-nitroarginine (both D- and L-isomers) at the N- and C-terminus with all of the natural amino acids (both D- and L-isomers) have been synthesized and tested for NOS inhibitory activity. The most potent inhibitors (based on isoform inhibition data) were L-nitroArg-L-Lys, L-nitroArg-L-nitroArg, L-Lys-D-nitroArg, D-Lys-D-nitroArg, L-His-D-nitroArg, L-nitroArg-D-Gln, D-nitroArg-L-Ser, and L-nitroArg-D-Asn. Dipeptides with unnatural amino acids also were made, and the most potent were L-nitroArg-L-Orn, L-nitroArg-L-2,4-diaminobutanoic acid, L-nitroArg-L-2,3-diaminopropanoic acid, and D-Orn-D-nitroArg. All of these dipeptides were dipeptide amides.

As part of these studies, over 70 dipeptides with $N^\omega$-nitroArg at the C-terminus have been synthesized and screened. None of these dipeptides significantly inhibited iNOS activity. Dipeptides containing non-charged alkyl side chains, such as Leu, Gly, Val, Met and Phe were good inhibitors of eNOS activity, especially the ones containing D-amino acid moieties. When the amino acids with aromatic moieties or amine (not amide) groups in the side chains (such as Phe, Lys, Arg, His and Trp) are coupled to nitroArg, the dipeptides were found to be somewhat better nNOS inhibitors. From these observations, it can be concluded that the primary amino side chain of Lys makes the Arg($NO_2$)-containing dipeptides selectively inhibit nNOS over eNOS.

IV. Pharmaceutical Compositions

The present invention also provides a pharmaceutical composition comprising an amino acid or dipeptide of this invention and a physiologically acceptable diluent. In a preferred embodiment, the present invention includes one or more NOS inhibitors as set forth above formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like.

The compositions can be administered to humans and animals either orally, rectally, parenterally, intracisternally, intravaginally, intraperitoneally, locally, or as a buccal or nasal spray.

Compositions suitable for parenteral administration can comprise physiologically acceptable sterile aqueous or non-aqueous solutions, dispersions, suspensions or emulsions and sterile powders for reconstitution into such sterile solutions or dispersions. Examples of suitable diluents include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

Compositions can also contain adjuvants such as preserving, wetting, emulsifying, and dispensing agents. Prevention of the action of microorganisms can be insured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form can be brought about by the use of agents delaying absorption, for example, aluminum monostearate and gelatin. Besides such inert diluents, the composition can also include sweetening, flavoring and perfuming agents. Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonit, agar—agar and tragacanth, or mixtures of these substances, and the like.

V. Methods of Inhibiting NOS Activity

In another aspect, the present invention provides a process for inhibiting the activity of at least one isoform of NOS. In accordance with one embodiment, one or more isoforms of NOS is exposed to an effective inhibitory amount of a derivative of Arg as set forth above.

In another embodiment a process of inhibiting NOS is accomplished by exposing one or more isoforms of NOS to an effective inhibitory amount of a dipeptide, dipeptide ester, dipeptide amide, or peptidomunetic analog that contains $N^\omega$-nitroArg or other unnatural amino acid as set forth above. When $N^\omega$-nitroArg is positioned at the C-terminus of the dipeptide, eNOS and nNOS activities are preferentially inhibited over iNOS. Where the dipeptide contains a neutral alkyl side chain (e.g., Leu, Gly, Val, Met, Phe), eNOS activity is preferentially inhibited.

The Examples that follow illustrate preferred embodiments of the present invention and are not limiting of the specification and claims in any way.

EXAMPLE 1

General Methods

Reagents.

$N^\alpha$-Box-ω-nitro-D-arg e and 2-(1H-benzotriazole-1-yl)-1,1,3,3-tetramethyluronium hexafluorophosphate (HBTU) were purchased from NOVA Biochemicals (San Diego, Calif.). $Arg^{NO2}$-Phe-OMe was purchased from BACHEM Feinchemikalien AG (Bubendorf, Switzerland) and was used without further purification. All other N-Box-L or D-amino acids and L- or D-amino acid esters were purchased from Sigma (St. Louis, Mo.). 1-(3-Dimethylaminopropyl)-3-ethylcarbodiimide (EDC), 1-hydroxybenzotriazole hydrate (HOBT), N,N-diisopropylethylamine (DIEA) and trifluoracetic acid (TFA) were obtained from Aldrich Chemical Co (Milwaukee, WI). Acids, bases, and conventional organic solvents were purchased from Fischer Scientific Co. L-Arginine, human ferrous hemoglobin AO, NADPH, $CaCl_2$, and calmodulin were purchased from Sigma Chemical Co. (St. Louis, MO). (6R)-5,6,7,8-Tetrahydro-L-biopterin ($BH_4$) was obtained from B. Schircks Laboratories (Jona, Switzerland) or from Alexis Biochemicals (San Diego, Calif.). Dithiothreitol (DTT) and Hepes were purchased from Fischer.

Enzyme Preparation.

nNOS was obtained from bovine brain as previously described (Furfine, E. S.; harmon, M. F.: Paith, J. E.; Garvey, E. P., *Biochemistry*, 1993, 32, 8512–8517). A typical preparation had a specific activity of 250 nmol of nitric oxide (mg of protein)$^{-1}$ min$^{-1}$. iNOS was purified according to the procedures of Hevel et al. Hevel, J. M.; Marletta, M. A., *Methods Enzymol,*. 1994, 233, 250–258 with a specific activity of 500 nmol of nitric oxide (mg of protein)$^{-1}$ h$^{1}$. eNOS, expressed in *E. coli*, was purified as described, Martasek, P.; Liu, Q.; Liu, J.; Roman, L. J.; Gross, S. S.; Sessa, W. C.; Masters, B. S. S., *Biochem. Biophys. Res. Commun.*, 1996, 219, 359–365.

Analytical Methods.

Nitric oxide formation was measured by using the hemoglobin capture assay. Hevel, J. M.; Marietta, M. A., *Methods Enzymol.*, 1994, 233-250-258. A typical assay mixture for nNOS contained 3–15 $\mu$M L-arginine, 1.6 mM $CaCl_2$, 11.6 $\mu$g,ml calmodulin, 100 $\mu$M DTT, 100 $\mu$M NADPH, 6.5 $\mu$M $BH_4$, and 3 mM oxyhemoglobin in 100 mM Hepes (pH 7.5). The reaction mixture for iNOS assay included 10–60 $\mu$M L-arginine, 100 $\mu$M DTT, 100 $\mu$M NADPH, 6.5 $\mu$M $BH_4$, and 3 mM oxyhemoglobin in 100 mM Hepes (pH 7.5). The production of nitric oxide by eNOS was measured as described. Sheta, E. A.; McMillan, K.; Masters, B. S. S. Evidence for a Bidomain Structure of Constitutive Cerebellar Nitric Oxide Synthase. *J. Biol. Chem.* 1994, 269, 15147–15153. Briefly, the assay mixture contained 80 $\mu$M oxyhemoglobin, 3–25 $\mu$M L-arginine, 100 $\mu$M DTT, 10 $\mu$M $CaCl_2$, 1 $\mu$g/mL calmodulin, 5 $\mu$M $BH_4$, 100 $\mu$M NADPH and 50 mM Hepes (ph 7.5). All assays were in a final volume of 600 $\mu$L and were initiated with enzyme. Nitric oxide reacts with oxyHb to yield methemoglobin which is detected at 401 nm ($\epsilon$=19700 M$^{-1}$cm$^{-1}$) (Feelish, M.; Noack, E. A., *Eur. J Pharmacol.*, 1987, 139, 19–30. on a Perkin-elmer Lambda 1 UV/vis spectrophotometer. Protein concentration of enzyme was determined with the Bradford Assay (Bio-Rad) using bovine serum albumin as the standard.

Optical rotation was determined with an AA-100 polarimeter (Optical Activity LTD, England) $^1$H-NMR spectra were recorded on a Varian Gemini-30$^6$ spectrometer in the solvent indicated. $^1$H-NMR chemical shifts in $D_2O$ are reported relative to internal sodium 3-(trimethylsilyl)-1-propanesulfonate (DSS). Fast atom bombardment (FAB) mass spectra were performed on a VG-Instruments 70–250-SE high resolution mass spectrometer. Elemental analyses were obtained from Oneida Research Services, Inc., Whitesboro, N.Y. Thin-layer chromatography was carried out on MercK silica gel 60-F254, 0.25 mm thickness. Amino acids were visualized with a ninhydrin/pyridine spray reagent or an UV/vis lamp. High-performance liquid chromatography was performed on a Beckman System Gold (Model 125P solvent module and Model 166 detector). Samples were analyzed by elution from a Vydac RP $C_{18}$90A (4×250 mm) pharmaceutical column with a flow rate of 0.75 mL/min. Samples (10 $\mu$L) were injected and eluted using the following gradient protocol: 0–5 min, solvent A (0.06% TFA in water); 5–60 min, linear gradient from solvent A to solvent B (0.05%TFA in acetonitrile).

EXAMPLE 2

Inhibition of NOS Activity by N-alkyl-L-Arg

Various N-alkyl-L-Arg and related derivatives were tested for their ability to inhibit NOS isoforms as set forth in Example 1. The results of those studies are summarized below in Table 1.

TABLE 1

Comparison of $K_i$ (or $IC_{50}$) Data for $N^\omega$-Substituted-L-Arginine Analogs of the
Formula R—NH—C(NH)NH—$(CH_2)_3$—CH(COO—)($NH_3$)

| | $K_i$ (nM) | | | Selectivity | |
|---|---|---|---|---|---|
| R | nNOS | iNOS | eNOS | nNOS/iNOS | nNOS/eNOS |
| propyl | 57 | 1.8 × 10$^5$ | 8500 | 3158 | 149 |
| allyl | 200 | 2100 | 3100 | 10.5 | 15.5 |
| propargyl | 430 | 620 | 810 | 1.4 | 1.9 |
| methyl$^e$ | 10000$^b$ | 14000$^b$ | 5900$^b$ | 1.4 | 0.6 |
| ethyl$^e$ | 16000$^b$ | 6100$^b$ | 9500$^b$ | 0.4 | 0.6 |

$^a$Selectivity for nNOS/iNOS is the ratio of the universe of the $K_i$ values, since the lower the $K_i$, the more potent the inhibition
$^b$$IC_{50}$ values, not $K_i$ values $N^\omega$-Propyl-L-arginine was found to be a potent and selective competitive inhibitor of neuronal nitric oxide synthase (nNOS) from bovine brain. Its $K_i$ for inhibition of nNOS is 3158 times lower than that for inhibition of recombinant murine macrophage nitric oxide synthase (iNOS) and 149 times lower than that for inhibition of recombinant bovine endothelial nitric oxide synthase (eNOS). This selectivity is unexpectedly much superior to that with four other closely-related structures, $N^\omega$-allyl-L-arginine, $N^\omega$-propargyl-L-arginine, $N^\omega$-methyl-L-arginine, and $N^\omega$-ethyl-L-arginine.

EXAMPLE 3

Inhibition of NOS Activity by Arg-Phe Dipeptides

Chemical Synthesis. N-Boc-dipeptide methyl ester.

N-Boc protected amino acid (1.5 mmol), was mixed at 0° C. (ice-water bath) in freshly distilled methylene chloride (4 mL). The suspension was stirred for 10 min to which was added dropwise DIEA (3.0 mmol) under $N_2$. The mixture was stirred for 2 h from 0° C. to room temperature. Shorten reaction time and concentrated reaction solution helped to minimize the chance of racemization. A large amount of water (30 mL) was added to quench the reaction, then the crude product was extracted with ethyl acetate (30 mL). After being washed sequentially with water (30 mL) 5% (v/v) HCl solution (2×20 mL), water (20 mL), 5% (w/v) $NaHCO_3$ solution (2×20 mL), water (20 mL) and saturated NaCl solution (20 mL), the organic layer was dried over $MgSO_4$. Crude protected dipeptide was obtained as a white powder by rotary evaporation of the ethyl acetate solution. The powder was dissolved in $CHCl_3$ and was loaded onto a silica gel column (3×50 cm). Pure N-Boc-dipeptide methyl ester was eluted with 20:1 $CHCl_3/CH_3OH$, monitoring by TLC. The yields were about 50%.

N-Boc-dipeptide benzyl ester.

To a stirred suspension of amino acid benzyl ester (1.5) mmol) and N-Boc-amino acid (1.3 equiv) in 2 mL of $CH_2Cl_2$ at 0° C. was added a methylene chloride solution (2 mL) of HBTU/HOBT (1.3 equiv each). After a few more minutes of stirring, 6 equiv of DIEA was added dropwise under $N_2$. The reaction mixture became homogenous after 2 h. Ethyl acetate was added to dilute the reaction solution, and the same work-up procedure was performed as described above.

Dipeptide Esters (Compounds 4–12).

The Boc groups of the methyl ester- and benzyl ester-protected dipeptides were removed by TFA or HCl (3 N in ethyl acetate). The Boc-protected amino acid ester was treated with acid (3 mL). The solution was stirred for 1 h (shorter time for HCl deprotection) under $N_2$. The acid was evaporated at room temperature, and the residue was dissolved in water (10 mL). The aqueous solution was washed with ethyl ether (3×10 mL) and the vacuum evaporated. When it was difficult to remove the water, the oily residue was dissolved in methanol and evaporated. The yield from the deprotection step was about 80%. The TFA or HCl salts of the dipeptide esters were used for all of the elemental analyses.

Dipeptides (compounds 1, 2, and 13 from Table 2.)

To a solution of N-Boc-dipeptide methyl ester (1 mmol) in methanol (5 mL) was added 1 N NaOH solution (10 mL). The mixture was stirred for 2 h at room temperature, then the methanol was evaporated. The aqueous solution was washed with ethyl acetate (2×10 mL) and was acidifed with 1 N citric acid. The precipitate that formed was extracted with ethyl acetate (2×20 mL). The extract was washed with water (2×20 mL) and was dried over $MgSO_4$. The N-Boc-dipeptide acid was obtained in a yield of 70% after evaporation of the solvent. A further deprotection of the Boc group by TFA or HCl was carried out as described above. Only D-Phe-D-Arge$^{NO2}$ was chromatographed on Dowex 50×8 (H$^+$ form) 200–400 mesh. The zwitterion was eluted with 0.25 N $NH_4OH$, lyophilized, and used for elemental analysis.

Chemistry.

All of the dipeptides were synthesized manually. HPLC indicated the presence of only one epimer for each compound, and all dipeptides were pure by NMR and elemental analysis and were optically active. A variety of other conditions led to epimerization in the product, which resulted in two product peaks (diastereomers) in the HPLC system used.

Inhibition Methods.

The reversible inhibition of NOS by the dipeptide analogs was studied under initial rate conditions with the hemoglobin assay as described above. The $K_i$ values were determined from Dixon plots (Dixon, M. The determination of enzyme inhibitor constants. *Biochem. J.* 1953, 55, 170–171). With various L-arginine and inhibitor concentrations. The type of reversible inhibition was determined from Cornish-Bowden replots of the data in the Dixon plots (Cornish-Bowden, A. A. Simple Graphical Method for Determining the Inhibition Constants of Mixed, uncompetitive and Non-Competitive Inhibitors. *Biochem J.* 1974 137, 143–144). The results of these studies are summarized below in Table 2.

TABLE 2

| Inhibitor | nNOS (µM) | iNOS (µM) | eNOS (µM) | nNOS/iNOS | nNOS/eNOS | iNOS/eNOS |
|---|---|---|---|---|---|---|
| 1. L-Arg$^{NO2}$-L-Phe | 18 | 160 | 395 | 8.9 | 21.9 | 2.5 |
| 2. L-Phe-L-Arg$^{NO2}$ | 140 | 93 | 490 | 0.66 | 3.5 | 5.3 |
| 3. L-Arg$^{NO2}$-L-Phe-OMe | 14 | 45 | 400 | 3.2 | 28.6 | 8.9 |
| 4. L-Phe-L-Arg$^{NO2}$-OMe | 370 | 204 | 1350 | 0.55 | 3.6 | 6.6 |
| 5. L-Arg$^{NO2}$-L-Phe-OBn | 55 | 18 | 125 | 0.33 | 2.3 | 6.9 |
| 6. L-Phe-L-Arg$^{NO2}$-OBn | 110 | 45 | 250 | 0.41 | 2.3 | 5.6 |
| 7. L-Arg$^{NO2}$-D-Phe-OMe | 92 | 100 | 525 | 1.1 | 5.7 | 5.3 |
| 8. D-Arg$^{NO2}$-L-Phe-OMe | 290 | 6400$^a$ | 1400 | 22.1 | 4.8 | 0.22 |
| 9. D-Arg$^{NO2}$-D-Phe-OMe | 150 | 6500$^a$ | 375 | 43.3 | 2.5 | 0.058 |
| 10. L-Phe-D-Arg$^{NO2}$-OMe | 90 | 7500$^a$ | 150 | 83.3 | 1.7 | 0.02 |
| 11. D-Phe-L-Arg$^{NO2}$-OMe | 400 | 1200 | 8500 | 3 | 21.3 | 7.1 |
| 12. D-Phe-D-Arg$^{NO2}$-OMe | 2 | 3600$^a$ | 5 | 1800 | 2.5 | 0.0014 |
| 13. D-Phe-D-Arg$^{NO2}$ | 17 | 13600$^a$ | 90 | 800 | 5.3 | 0.0066 |

$^a$Uncompetitive inhibition

All of the dipeptides and dipeptide esters were competitive inhibitors of the three isoforms of NOS, except for the ones that contain D-Arg$^{NO2}$ (compounds 8–10, 12, 13), which were uncompetitive inhibitors of iNOS, but competitive inhibitors of nNOS and eNOS (Table 2). None of the dipeptides or dipeptide esters tested (1, 2, 12, 13) exhibited time-dependent inhibition of any of the isoforms, unlike N-nitro-L-arginine itself, which had $K_I$ and $k_{inact}$ values of 9.3 µM and 0.132 min$^{-1}$, respectively with nNOS. None of the kinetic plots showed curvature, suggesting that there was no time dependence to the inhibition.

The order of the amino acids in the dipeptide is important to selectivity, but it depends on the chirality of the amino acids. Thus, for the dipeptide and dipeptide methyl ester pairs compound 1 vs compound 2 and compound 3 vs compound 4, having L-nitroArg at the N-terminus favors nNOS over iNOS and eNOS inhibition, but when the L-Phe is at the N-terminus, it favors iNOS over nNOS and eNOS inhibition. In the case of the corresponding benzyl ester (compound 5 vs compound 6), both dipeptides favor iNOS over nNOS and eNOS inhibition. All of the dipeptide methyl esters containing a D-amino acid, however, exhibit an inhibitory preference for nNOS over iNOS and eNOS. The most impressive selectivities observed are 1 800-fold and 800-fold for compound 12 and compound 13, respectively, in favor of nNOS over iNOS. These results indicate that there is a difference in the binding sites of nNOS vs iNOS that can be taken advantage of by appropriate design of D-amino acid-containing peptide esters. The selectivity of these analogs for nNOS over eNOS is only 2.5 and 5.3, respectively. The selectivity of eNOS over iNOS for compound 12 and compound 13, however, are 714- and 152-fold, respectively. Because of the unnatural chirality of the amino acids and the incorporation of an ester functionality, the most nNOS vs iNOS-selective compounds are peptidomimetic analogs, which may make them orally bioavailable. The enormous selectivity of compounds of compound 12 and compound 13 suggests that other dipeptides and dipeptide esters of unnatural amino acids should be tested.

EXAMPLE 4
Inhibition of NOS by Dipeptides that Contain Nω-nitroArg

An entire series of dipeptide amides containing Nω-nitroarginine (both D- and L-isomers) at the N- and C-terminus with all of the natural amino acids (both D- and L-isomers) have been synthesized and tested for NOS inhibitory activity according to the procedures of Examples 1 and 2. The results of these studies are summarized below in Table 3.

chains, such as Leu, Gly, Val, Met and Phe were good inhibitors of eNOS activity, especially the ones containing D-amino acid moieties. When the amino acids with aromatic moieties or amine (not amide) groups in the side chains (such as Phe, Lys, Arg, His and Trp) are coupled to nitroArg, the dipeptides were found to be somewhat better nNOS inhibitors. From these observations, it can be concluded that the primary amino side chain of Lys makes the nitroArg-containing dipeptides selectively inhibit nNOS over eNOS.

TABLE 3

| | | N-Terminus $(NO_s)$-Arg | | | | | | C-Terminus $(NO_s)$-Arg | | | | | |
|---|---|---|---|---|---|---|---|---|---|---|---|---|---|
| | | L-Isomer | | | D-Isomer | | | L-Isomer | | | D-Isomer | | |
| AA | L/D | nNOS | eNOS | iNOS | nNOS | eNOS | iNOS | nNOS | eNOS | iNOS | nNOS | eNOS | iNOS |
| Tyr | L | 50 | 95 | 97 | 94 | 90 | 94 | 98 | 93 | 101 | 63 | 93 | 92 |
| | D | 88 | 98 | 93 | 88 | 93 | 92 | 88 | 91 | 83 | 46 | 39 | 87 |
| Thr | L | 68 | 92 | 86 | 91 | 95 | 79 | 87 | 91 | 91 | 62 | 80 | 89 |
| | D | 63 | 83 | 84 | 87 | 92 | 95 | 87 | 92 | 79 | 57 | 69 | 83 |
| Met | L | 53 | 100 | 92 | 87 | 92 | 94 | 91 | 87 | 94 | 67 | 85 | 92 |
| | D | 54 | 90 | 84 | 93 | 101 | 96 | 87 | 96 | 80 | 36 | 24 | 78 |
| Asp | L | 95 | 93 | 92 | 80 | 86 | 97 | 91 | 89 | 93 | 87 | 89 | 86 |
| | D | 87 | 91 | 96 | 84 | 84 | 97 | 89 | 97 | 83 | 81 | 90 | 80 |
| Nitro-Arg | L | | | | | | | 12 | 81 | 66 | 40 | 72 | 70 |
| | D | | | | | | | 57 | 70 | 79 | 33 | 25 | 77 |
| Ser | L | 53 | 89 | 91 | 13 | 92 | 94 | 87 | 99 | 93 | 60 | 91 | 101 |
| | D | 43 | 90 | 89 | 73 | 89 | 95 | 84 | 96 | 98 | 59 | 84 | 90 |
| Pro | L | 86 | 88 | 85 | 94 | 93 | 84 | 72 | 95 | 97 | 37 | 65 | 99 |
| | D | 93 | 97 | 85 | 99 | 94 | 84 | 76 | 90 | 97 | 46 | 57 | 91 |
| Ala | L | 66 | 86 | 73 | 82 | 89 | 81 | 91 | 97 | 95 | 60 | 88 | 96 |
| | D | 51 | 83 | 73 | 71 | 82 | 77 | 81 | 94 | 90 | 56 | 68 | 89 |
| Leu | L | 66 | 96 | 77 | 94 | 102 | 97 | 88 | 98 | 97 | 66 | 95 | 98 |
| | D | 66 | 94 | 90 | 95 | 95 | 100 | 93 | 96 | 97 | 32 | 13 | 83 |
| Lys | L | 6 | 96 | 72 | 63 | 96 | 97 | 78 | 99 | 91 | 21 | 98 | 97 |
| | D | 27 | 97 | 84 | 72 | 96 | 97 | 67 | 99 | 87 | 14 | 84 | 84 |
| His | L | 35 | 89 | 82 | 77 | 97 | 93 | 94 | 85 | 97 | 38 | 90 | 99 |
| | D | 60 | 93 | 84 | 67 | 98 | 86 | 83 | 96 | 95 | 66 | 86 | 90 |
| Val | L | 48 | 88 | 86 | 87 | 96 | 87 | 86 | 93 | 87 | 66 | 86 | 92 |
| | D | 47 | 99 | 79 | 87 | 101 | 85 | 91 | 95 | 97 | 50 | 32 | 87 |
| Trp | L | 48 | 91 | 79 | 81 | 98 | 80 | 95 | 93 | 88 | 59 | 84 | 86 |
| | D | 71 | 77 | 82 | 86 | 83 | 89 | 82 | 86 | 81 | 43 | 54 | 79 |
| Gln | L | 37 | 85 | 62 | 82 | 77 | 85 | | | | 76 | 84 | 85 |
| | D | 23 | 88 | 65 | 84 | 80 | 93 | 93 | 93 | 100 | 58 | 57 | 95 |
| Gly | L | 47 | 95 | 89 | 85 | 98 | 105 | 93 | 81 | 94 | 51 | 60 | 102 |
| | D | | | | | | | | | | | | |
| Ile | L | 62 | 81 | 92 | 93 | 94 | 95 | 60 | 88 | 98 | 66 | 79 | 104 |
| | D | | | | | | | | | | | | |
| Cys | L | 52 | 96 | 97 | 88 | 93 | 99 | 98 | 90 | 102 | 72 | 83 | 109 |
| | D | | | | | | | | | | | | |
| Glu | L | 84 | 77 | 97 | 89 | 90 | 93 | 90 | 84 | 109 | 84 | 81 | 102 |
| | D | 88 | 90 | 89 | 81 | 93 | 99 | | | | | | |
| Asn | L | 44 | 83 | 65 | 81 | 85 | 80 | 87 | 85 | 110 | 52 | 84 | 92 |
| | D | 3 | 81 | 19 | 74 | 86 | 78 | 87 | 75 | 97 | 69 | 77 | 93 |
| Dpr | L | 20 | 91 | 61 | 58 | 86 | 70 | 78 | 93 | 76 | 49 | 80 | 86 |
| | D | | | | | | | | | | | | |
| Dbu | L | 2 | 89 | 36 | 35 | 74 | 82 | 72 | 94 | 84 | 31 | 85 | 75 |
| | D | | | | | | | | | | | | |
| Orn | L | 4 | 95 | 51 | 41 | 88 | 87 | 72 | 89 | 95 | 27 | 89 | 98 |
| | D | 27 | 104 | 81 | 65 | 104 | 98 | 51 | 95 | 93 | 35 | 89 | 96 |

The most potent inhibitors (based on isoform inhibition data) were L-nitroArg-L-Lys, L-nitroArg-L-nitroArg, L-Lys-D-nitroArg, D-Lys-D-nitroArg, L-His-D-nitroArg, L-nitroArg-D-Gln, D-nitroArg-L-Ser, and L-nitroArg-D-Asn. Dipeptides with unnatural amino acids also were made, and the most potent were L-nitroArg-L-Orn, L-nitroArg-L-2,4-diaminobutanoic acid, L-nitroArg-L-2,3-diaminopropanoic acid, and D-Orn-D-nitroArg. All of these dipeptides were dipeptide amides.

As part of these studies, over 70 dipeptides with $N^{ω}$-nitroArg at the C-terminus have been synthesized and screened. None of these dipeptides significantly inhibited iNOS activity. Dipeptides containing non-charged alkyl side

What is claimed is:

1. A method of inhibiting the activity of neuronal nitric oxide synthase comprising contacting neuronal nitric oxide synthase with a dipeptide for a time and under conditions effective to inhibit the activity of neuronal nitric oxide synthase, wherein at least one of the two amino acids in the dipeptide is D- or L-Nitroarginine or an ester or amide derivative thereof.

2. The method of claim 1 wherein the dipeptide is L-Nitroarginine-L-Phe-OMe, L-Nitroarginine-D-Phe-OMe, D-Nitroarginine-L-Phe-OMe, D-Nitroarginine-D-Phe-OMe, D-Phe-L-Nitroarginine-OMe, L-Phe-D-Nitroarginine-OMe, D-Phe-D-Nitroarginine-OMe, L-Phe-L-Nitroarginine-OMe, L-Nitroarginine-L-Phe-OBn or L-Phe-L-Nitroarginine-OBn, D-Phe-L-Nitroarginine, L-Nitroarginine-L-Phe, L-Phe-L-Nitroarginine, L-N$^\omega$-nitroarginine-L-lysine, L-N$^\omega$-nitroarginine-L-N$^\omega$-nitroarginine, L-lysine-D-N$^\omega$-nitroarginine, D-lysine-D-N$^\omega$-nitroarginine, L-histidine-D-N$^\omega$-nitroarginine, L-N$^\omega$-nitroarginine-D-glutamine, D-N$^\omega$-nitroarginine-L-serine, L-N$^\omega$-nitroarginine-D-asparagine, L-nitroArg-L-2,4-diaminobutanoic acid, L-nitroArg-L-Orn, L-nitroArg-L-2,3-diaminopropanoic acid, or D-Orn-D-nitroArg.

3. A process for selectively inhibiting the activity of endothelial nitric oxide synthase and neuronal nitric oxide synthase relative to inducible nitric oxide synthase comprising exposing endothelial nitric oxide synthase, neuronal nitric oxide synthase and inducible nitric oxide synthase to an amino acid derivative of the formula N$^\omega$-R-L-Arginine, where R is a $C_2$–$C_6$ alkane or alkene for a time and under conditions effective to selectively inhibit the activity of endothelial nitric oxide synthase and neuronal nitric oxide synthase relative to inducible nitric oxide synthase.

4. The process of claim 3, where R is ethyl, propyl, or allyl.

5. A composition comprising a suitable diluent and a dipeptide, wherein the dipeptide is present in an amount effective to inhibit nitric oxide synthase, and wherein the dipeptide is selected from the group consisting of L-Nitroarginine-L-Phe-OMe, L-Nitroarginine-D-Phe-OMe, D-Nitroarginine-L-Phe-OMe, D-Nitroarginine-D-Phe-OMe, D-Phe-L-Nitroarginine-OMe, L-Phe-D-Nitroarginine-OMe, D-Phe-D-Nitroarginine-OMe, L-Phe-L-Nitroarginine-OMe, L-Nitroarginine-L-Phe-OBn, L-Phe-L-Nitroarginine-OBn, D-Phe-L-Nitroarginine, L-Nitroarginine-L-Phe, L-Phe-L-Nitroarginine, L-N$^\omega$-nitroarginine-L-lysine, L-N$^\omega$-nitroarginine-L-N$^\omega$-nitroarginine, L-lysine-D-N$^\omega$-nitroarginine, D-lysine-D-N$^\omega$-nitroarginine, L-histidine-D-N$^\omega$-nitroarginine, L-N$^\omega$-nitroarginine-D-glutamine, D-N$^\omega$-nitroarginine-L-serine, L-N$^\omega$-nitroarginine-D-asparagine, L-nitroArg-L-2,4-diaminobutanoic acid, L-nitroArg-L-Orn, L-nitroArg-L-2,3-diaminopropanoic acid, and D-Orn-D-nitroArg.

6. A composition comprising a suitable diluent and an amino acid derivative of the formula N$^\omega$-propyl-L-Arginine, wherein the amino acid derivative is present in an amount effective to inhibit nitric oxide synthase.

7. A process for selectively inhibiting the activity of neuronal nitric oxide synthase relative to endothelial nitric oxide synthase and inducible nitric oxide synthase comprising exposing endothelial nitric oxide synthase, neuronal nitric oxide synthase and inducible nitric oxide synthase to an amino acid derivative of the formula N$^\omega$-R-L-Arginine, where R is a $C_2$–$C_6$ alkane or alken for a time and under conditions effective to selectively inhibit the activity of neuronal nitric oxide synthase relative to endothelial nitric oxide synthase and inducible nitric oxide synthase.

* * * * *